United States Patent [19]

Mrozik

[11] 4,064,239

[45] Dec. 20, 1977

[54] HALOGENATED UNSATURATED ALKYL BENZENEDISULFONAMIDES AS ANTHELMINTICS

[75] Inventor: Helmut H. Mrozik, Matawan, N.J.

[73] Assignee: Merck & Co., Inc., Rahway, N.J.

[21] Appl. No.: 616,331

[22] Filed: Sept. 26, 1975

Related U.S. Application Data

[63] Continuation-in-part of Ser. No. 533,352, Dec. 16, 1974, abandoned.

[51] Int. Cl.$^2$ .................... C07C 143/80; A61K 31/63
[52] U.S. Cl. ........................ 424/228; 260/397.7 DS; 260/556 B; 260/556 S; 260/347.2; 260/268 PH; 424/321; 544/59; 544/152; 544/159
[58] Field of Search ...... 260/556 B, 556 S, 397.7 DS; 424/228

[56] References Cited

U.S. PATENT DOCUMENTS

| | | | |
|---|---|---|---|
| 3,009,910 | 11/1961 | Ziegler | 260/556 S X |
| 3,139,381 | 6/1964 | Novello | 260/556 S X |
| 3,163,644 | 12/1964 | de Stevens et al. | 260/556 S X |
| 3,164,517 | 1/1965 | Novello | 260/556 S X |
| 3,287,360 | 11/1966 | Novello | 260/397.7 DS X |
| 3,297,693 | 1/1967 | de Stevens et al. | 260/397.7 DS X |
| 3,821,276 | 6/1974 | Mrozik et al. | 424/228 X |

FOREIGN PATENT DOCUMENTS

| | | | |
|---|---|---|---|
| 250,932 | 4/1964 | Australia | 260/556 S |
| 210,873 | 8/1960 | Austria | 260/556 S |

OTHER PUBLICATIONS

Sprague et al., CA 58:P12586C, (1963).
Cragoe et al., CA 58:12564d, (1963).

*Primary Examiner*—Daniel E. Wyman
*Assistant Examiner*—Thomas A. Waltz
*Attorney, Agent, or Firm*—David L. Rose; J. Jerome Behan

[57] ABSTRACT

Novel substituted benzenedisulfonamides are disclosed which compounds are active anthelmintic agents being particularly useful against fascioliasis in sheep and cattle. Specifically the active compounds are 4-amino-1,3-benzenedisulfonamide with an unsaturated substituted alkyl group. Compositions and methods containing the novel substituted benzenedisulfonamides for use in anthelmintic therapy particularly against liver fluke are also disclosed.

13 Claims, No Drawings

HALOGENATED UNSATURATED ALKYL BENZENEDISULFONAMIDES AS ANTHELMINTICS

RELATIONSHIP TO OTHER APPLICATIONS

This application is a continuation-in-part application of U.S. Ser. No. 533,352, filed Dec. 16, 1974 now abandoned.

DESCRIPTION OF THE PRIOR ART

Many sulfonamides, especially benzenedisulfonamide compounds have been known in the art for many years. They have been generally prepared and studied for their activity as antibacterial and diuretic agents and much data is published concerning the bacteriostatic and diuretic activity of sulfonamide compounds. In addition, certain benzenedisulfonamides have been prepared as intermediates in the preparation of diuretic agents having substantial diuretic activity. Said diuretic agents have not been disclosed as having any anthelmintic activity. The instant benzenedisulfonamides, however, are novel compounds not having been disclosed in the prior art.

SUMMARY OF THE INVENTION

The novel anthelmintic compounds of this invention are classified generally as benzenedisulfonamides. Specifically they may be described as 4-amino-6-substituted-1,3-benzenedisulfonamides. Said compounds have significant and unexpected anthelmintic activity and in particular demonstrate high activity against Fasciola or liver fluke in animals. The instant compounds also possess significant parasiticidal activity.

Thus, it is an object of this invention to provide for novel anthelmintic compounds. A further object of this invention is to provide for novel substituted benzenedisulfonamide compounds which have significant anthelmintic and fasiolicidal activity. A still further object of this invention is to provide for processes for the preparation of said novel substituted benzenedisulfonamides. Another object is to provide for compositions and methods of treatment which contain said novel substituted benzenedisulfonamides, and which are useful in the prevention and treatment of fascioliasis. Further objects will become apparent from the following description.

DESCRIPTION OF THE INVENTION

The compounds of this invention which are active anthelmintic agents and best described by the following structural formula:

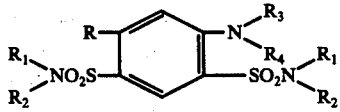

I wherein
Each $R_1$ and $R_2$ are each hydrogen or loweralkyl, R is a halogenated unsaturated alkyl group containing from 2 to 6 carbon atoms, one or two double bonds or single triple bond and from 1 to 11 halogen atoms, and $R_3$ and $R_4$ are independently hydrogen, loweralkyl, benzyl furfuryl or phenyl; or $R_3$ and $R_4$ may be joined to form a heterocyclic group of $N^4$-loweralkyl piperazine, morpholine or thiomorpholine-1,1-dioxide.

The term "loweralkyl" refers to those alkyl groups having from 1 to 5 carbon atoms in a straight or branched configuration.

The preferred compounds of this invention are realized when R is a carbon chain of from 2 to 4 carbon atoms containing a single double bond and from 2 to 6 halogen atoms.

The most preferred compounds of this invention are realized when the halogen atoms on the R group are chlorine or fluorine or a mixture thereof.

Examples of the most preferred compounds of this invention are:

4-amino-6-trichlorovinyl-1,3-benzenedisulfonamide
4-amino-6-($\alpha,\beta$-difluoro-$\beta$-chlorovinyl-1,3-benzenedisulfonamide
4-amino-6-($\alpha,\beta$-dichloro-$\beta$-fluorovinyl)-1,3-benzenedisulfonamide
4-amino-6-trifluorovinyl-1,3-benzenedisulfonamide.

The compounds of this invention wherein $R_3$ and $R_4$ are hydrogen are generally prepared by a process outlined in the following reaction scheme:

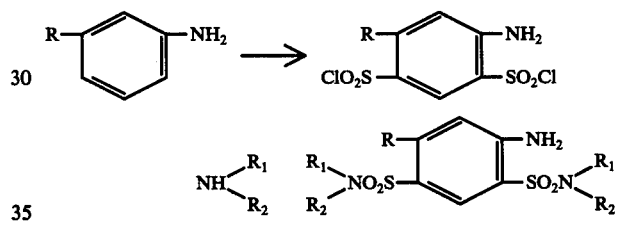

wherein R, $R_1$ and $R_2$ are as previously defined.

In the first step of this process an appropriately substituted aniline compound is treated with chlorosulfonic acid. The reaction is carried out initially with external cooling due to a possible exothermic reaction as the starting material and the reagent are combined. Generally the amine is added dropwise or portionwise over a period of from 5 minutes to 2 hours, to the chlorosulfonic acid maintaining the reaction temperature at from $-10°$ to $10°$ C. When the addition is complete, the reaction temperature is raised to from =° to 200° C. for from 15 minutes to 4 hours. A solvent is optional and generally employed only when the reaction temperature is below 100° C. It is preferred, however, to run the reaction without a solvent. The product benzenedisulfonylchloride is recovered from the reaction mixture by procedures known to those skilled in this art.

The benzenedisulfonyl chloride is then reacted with ammonia or a mono or diloweralkylamine to form the desired benzenedisulfonamide. The reaction may be carried out with aqueous solutions of ammonia or the mono or di-loweralkylamine, non aqueous solutions of ammonia or the mono or diloweralkylamine in any non reactive organic solvent such as benzene, toluene, ether, chloroform and the like; or the reaction may be carried out in liquid ammonia or amine. The reaction is somewhat exothermic and when an amine other than liquid ammonia is employed, external cooling is required. In liquid ammonia the reaction mixture is maintained at the temperature of liquid ammonia. The product is isolated and purified by techniques known to those skilled in this art.

The compounds of this invention may also be prepared by chlorosulfonating an appropriately substituted O-amino benzenesulfonamide compound followed by amination as outlined in the following reaction scheme:

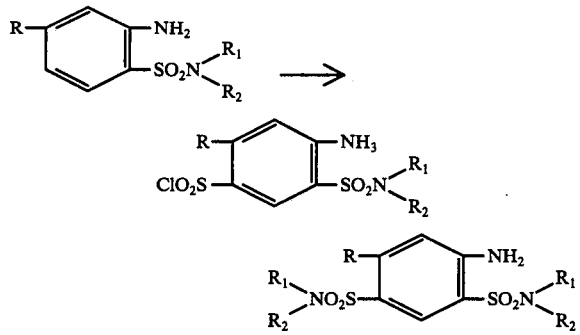

wherein R, R and R are as previously defined. Chlorosulfonic acid is generally preferred as the chlorosulfonating agent following the procedures outlined above. The chlorosulfonic acid is then treated with ammonia or a mono- or di- loweralkylamine in the manner previously defined to obtain the desired product. The product is isolated by techniques known to those skilled in this art. It is readily apparent that the above described process is capable of producing compounds wherein the —$NR_1R_2$ groups on each of the sulfonamide moieties is different from the other.

The compounds of this invention wherein $R_3$ and $R_4$ are other than hydrogen are prepared from the compounds wherein $R_3$ and $R_4$ are hydrogen by the following procedure:

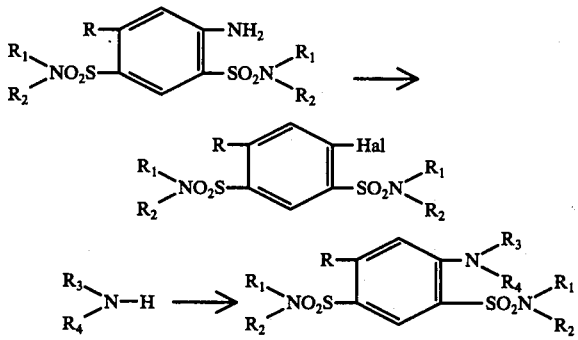

wherein R, $R_1$, $R_2$, $R_3$ and $R_4$ are as previously defined, and Hal is a halogen, particularly chloro or bromo.

In the foregoing procedure the unsubstituted amino starting material is diazotized with an alkali metal nitrite, particularly sodium nitrite, in the presence of an acid, and the diazonium salt treated with an alkaline earth halide affording the 4-halo compound. The diazotization is generally run in an aqueous medium at from 0° to 25° C. and the preferred acids are sulfuric nitric and acetic.

The diazotized compound, still in aqueous medium, is combined with an alkaline earth metal halide in a hydro halide acid solution wherein the halide of the salt and the acid are the same. The addition, at from 0° C. to room temperature, is complete in from 5 minutes to 1 hour and the reaction mixture is optionally stirred for an additional period of time, conveniently up to 2 hours.

The halide is isolated by techniques known to those skilled in this art.

The halo compound is converted to the $R_3$, $R_4$ substituted amino compound by treatment with an $R_3$, $R_4$ substituted amine. The reaction is carried out by heating at from 25° to 200° C., however, it is preferred to heat at from 75° to 125° C. The reaction is complete in from 15 minutes to 24 hours and the product isolated by techniques known to those skilled in this art.

The starting materials for the foregoing procedures are generally known in the art or procedures are published in the art which would enable one skilled in the art to readily prepare said starting materials.

The meta substituted aniline of first described synthesis wherein R is an unsaturated halogenated alkyl group in which the unsaturation is in the $\alpha\beta$ position relative to the benzene ring, may be prepared according to the following reaction scheme:

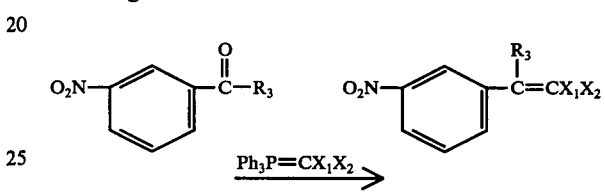

wherein Ph is phenyl, $R_3$ is hydrogen, loweralkyl or halogenated loweralkyl; and $X_1$ and $X_2$ are each halogen.

The starting material for this process is a m-nitro benzaldedyle or a m-nitro phenyl-loweralkyl or halo-loweralkyl ketone. The reagent $(Ph)_3 P=CX_1X_2$ is prepared by coupling triphenyl phosphine with a halogenated methane such as carbon tetrachloride, carbon tetrabromide, chloroform, bromoform and the like. The reagent is not isolated but rather prepared in situ. The preferred method is to combine all of the starting materials, the triphenyl phosphine, the halogenated methane and the benzaldehyde or ketone in a single reaction vessel at a temperature of from room temperature to 200° C. Since the phosphorous reagent is prepared in situ, the starting material is readily available for reaction avoiding problems of storage and stability of the reagent. The reaction mixture is maintained within the above temperature range for from 1 to 24 hours and the product isolated by techniques known to those skilled in this art. The halogenated methane is generally used in excess so that no additional solvent is required, however, a non reactive solvent could optionally be employed.

The nitro compound of the above reaction is then reduced to the corresponding amino compound using reduction techniques such as iron and hydrochloric acid or zinc and acetic acid. The amino compound thus obtained is treated with chlorosulfonic acid followed by ammonia according to the procedures already described to obtain the desired product.

A variation of the above method starts with the readily available unsubstituted benzaldehyde or phenyl loweralkyl or halogenated loweralkyl ketone:

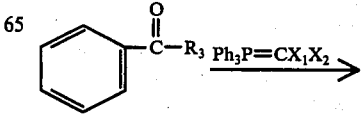

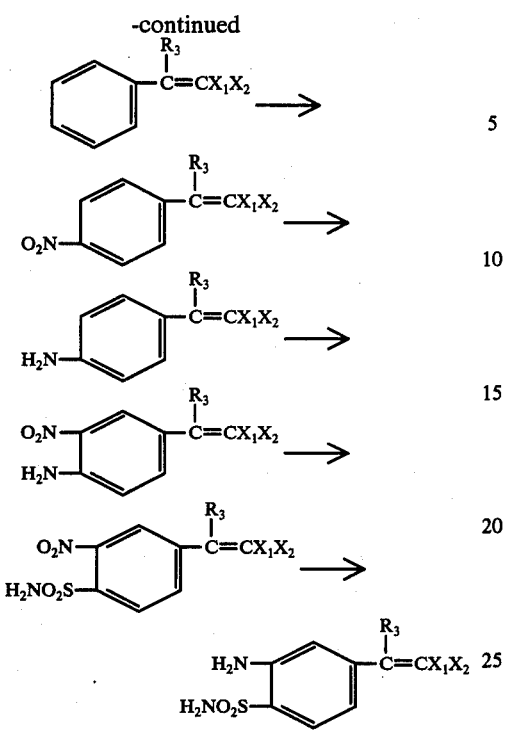

wherein Ph, $R_3$, $X_1$ and $X_2$ are as previously defined.

Benzaldehyde or the ketone is treated with the $Ph_3P=C(R)_2$ reagent according to the procedures set forth above. The halogenated vinyl or propenyl compound thus produced is then nitrated. The nitration is p-directing and thus the p-nitro compound is recovered. The reaction is run in excess nitrating agent such as nitric acid, fuming nitric acid and the like in the presence of a dehydrating agent such as concentrated sulfuric acid, acetic anhydride and the like. The reaction mixture is maintained at from 0° to 50° C. for from 15 minutes to 3 hours. The product is isolated from the nitration reaction mixture by techniques known to those skilled in this art.

The nitrated compound is then reduced to the corresponding amino compound using standard reduction techniques. In order to facilitate subsequent steps in the synthesis, however, the amino group is generally protected with a suitable protecting group such as an acyl, preferably acetyl, function. The amino group is acylated with any of the standard acylating reagents available such as acid chlorides, anhydrides, carboxylic acids and the like which correspond to the desired protecting group.

The protected amine compound is then nitrated using the nitration techniques described above. The compound recovered is the m-nitro, p-amino compound. After the nitration the protecting group is removed using standard techniques known to those skilled in the art. In the case of acyl protecting groups, acid or base catalyzed hydrolysis readily recovers the free amine.

The free amine is then diazotized to prepare the sulfonamide group.

The amine compound is diazotized in the presence of aqueous acid such as hydrochloric or sulfuric acid and sodium nitrite at from 0° to 20° C. The diazonium salt is then treated with a solution of sulfur dioxide and crystalline cupric chloride in acetic acid and sufficient water to effect solution. The reaction mixture is maintained at from 0° to 20° C. for from 5 minutes to 3 hours. The sulfonyl chloride group thus isolated from the diazotization reaction is treated with ammonia or a mono or di-loweralkylamine as described above affording the mono sulfonamide which is chloro sulfonated and aminated as described above.

A still further process for the preparation of the 3-R-aniline starting materials utilizes m-nitro aniline as precursor. The m-nitro aniline is diazotized with a mineral or organic acid, sodium nitrite and water as is fully described above. The diazonium salt is then treated with an ethylene compound of the formula:

$$R_4R_5C=CHX$$

in the presence of crystalline cupric chloride dihydrate and acetone of other suitable non-reactive organic solvent. In the above formula X is halogen and $R_4$ and $R_5$ are each halogen or one of $R_4$ and $R_5$ may be halogen and the other is hydrogen, loweralkyl or halogenated loweralkyl. The reaction is conducted initially at from $-20°$ to 20° C. and following the initial reaction is maintained substantially at room temperature for from 1 to 48 hours to complete the reaction. The resultant product has the formula:

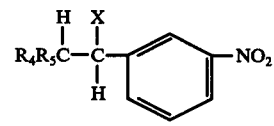

wherein X, $R_4$ and $R_5$ are as defined above. This compound is then dehydrohalogenated to form:

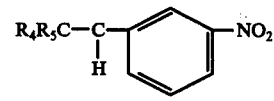

wherein $R_4$ and $R_5$ are as previously defined. The dehydrohalogenation is carried out using an alkali metal hydroxide or alkoxide or an organic base such as triethylamine in the presence of a suitable solvent such as a loweralkanol, preferably methanol or ethanol. The nitro group is then reduced using the reduction techniques described above and the resultant amino compound chlorosulfonated and aminated. Optionally the chlorosulfonation and amination reactions may be conducted before the diazotzation and dehydrohalogenation reaction steps. Specifically 2-(3-aminophenyl)-1,1,2-trichloroethylene is best prepared from the known starting material 2-(3-aminophenyl) 1,1,1,2,2-pentachloroethane which is dehalogenated using zinc in ethanol utilizing the above reaction conditions. The foregoing process is also applicable to the production of other compounds wherein the unsaturation is at any other carbon atoms by utilizing the appropriate starting materials.

The compounds of the present invention have utility in the field of animal therapy. They are effective against both mature and immature liver fluke of the species *Fasciola gigantica* and *Fasciola hepatica*, the common liver fluid in sheep and cattle. The preferred dosage levels depend on the type of compound to be employed, the type of animal to be treated, the particular helminth to be combatted, and the severity of the halminthic infestation. In general, effective fluke eradication is achieved when the compounds are administered in a single dose at dosage levels of from about 1 to 150 mg/kg of animal body weight and preferably from about 1 to 50 mg/kg of animal body weight. The compounds of the present invention may be administered in a variety of ways depending upon the particular animal employed, the type of anthelmintic treatment normally given to such animal, the materials employed and the particular helminths being combatted. It is preferred to administer them in anthelmintically effective amounts in a single or divided oral or parenteral dose at a time when fluke infection is apparent or suspected in the animal.

In addition to the inactive ingredients in the composition, said composition may contain one or more other active ingredients which may be selected from the compounds of formula I or from other known anthelmintic agents. Beneficial results are obtained when the compounds of formula I are combined with an anthelmintic agent such as 2-(4-thiazolyl)benzimidazole (thiabendazole) or tetramisole (dl-2,3,5,6-tetrahydro-6-phenylimidazo[2,1-b]thiazole) or other known anthelmintic agents.

In general, composition containing the active anthelmintic compound are employed. The amounts of the anthelmintic ingredient in the composition as well as the remaining constituents vary according to the type of treatment to be employed, the host animal and the particular helmintic infestation being treated. In general, however, compositions suitable for oral administration, containing a total weight percent of the active compound or compounds ranging from 0.01 to 95% will be suitable with the remainder of the compositions being any suitable carrier or vehicle. A number of modes of treatment may be employed and each to some extent determines the general nature of the composition. For example, the anthelmintic compounds may be administered to domesticated animals in a unitary oral dosage form such as a tablet, bolus, capsule, or drench; a liquid oil base form suitable for parenteral administration, or they may be compounded as a feed premix to be later admixed with the animal food. When the compositions are to be solid unit dosage forms as in tablets, capsules, or boluses, the ingredients other than the active compounds may be any other non-toxic vehicle convenient in the preparation of such forms and preferably materials nutritionally suitable such as starch, lactose, talc, magnesium stearate, vegetable gums, and the like. Moreover, when capsules are employed, the active compound may be used in essentially undiluted form, the only extraneous material being that of the capsule casing itself which may be hard or soft gelatin or any other orally acceptable encapsulating material. When the dosage form is to be used for parenteral administration the active material is suitably admixed with an acceptable oil base vehicle preferably of the vegetable oil variety such as peanut oil, cotton seed oil, and the like. In all such forms, that is, in tablets, boluses, capsules, and oil base formulations; the active compound conveniently ranges from about 5 to 95% by weight of the total composition.

When the unit dosage form is to be in the form of a drench, the anthelmintic agents may be mixed with agents which will aid in the subsequent suspending of the active compounds in water such as bentonite, clays, water soluble starches, cellulose derivatives, gums, surface active agents and the like to form a dry pre-drench composition, and this pre-drench composition is added to water just before use. In the pre-drench formulation, in addition to the suspending agent, such ingredients as preservatives, anti-foam compounds, or other suitable diluents or solvents may be employed. Such a dry product may contain as much as 95% by weight of the active compound, the rest being excipient. Preferably, the solid composition contains from 30 to 95% by weight of the active compound. Enough water should be added to the solid product to provide proper dosage level with a convenient amount of liquid for a single oral dose. The commonly used measure in the field is 1 fluid ounce of material and thus that 1 fluid ounce of material should contain enough of the anthelminitic compound to provide an effective dosage level. Liquid drench formulations containing from 10 to 50% by weight of dry ingredients will, in general, be suitable with a preferred range being from 15 to 25 weight percent.

When the compositions are intended to be used in feeds, feed supplements or feed premixes, they will be mixed with suitable ingredients of the animals nutrient ration. Solid orally ingestible carriers normally used for such purposes such as distiller dried grans, corn shells, citrus meal, attapulgus clay, wheat shorts, molasses solubles, corn cob meal, vegetable substances, toasted dehulled soya flour, soya bean meal feed, antibiotic mycellia, soya grits, crushed limestone and the like are all suitable. The active compounds are intimately dispersed or admixed throughout the active solid carrier by methods as grinding, melting, or tumbling. By selecting a proper diluent and by altering the ratio of carrier to active ingredient, compositions of any desired concentration may be prepared. Feed supplement formulations containing from about 5 to 30% of active ingredient are particularly suitable for addition to feeds. The active compound is normally dispersed or mixed uniformly in the diluent but in some instances may be absorbed on the carrier.

These supplements are added to the finished animal feed in an amount adequate to give the final concentration desired for controlling or treating the helminth infection by way of animal ration. Although the preferred level in feeds will depend on the particular compounds being employed, the active compounds of this invention are normally feed at levels of 0.01 to 3%. As stated above, animals are preferably treated at a time when the infestation is apparent or suspected and the most preferred method of treatment is with oral doses. Thus, administration of medicated feed is not preferred but may be employed. Similarly, the amounts of drug present in the feed may be reduced to levels in the order of 0.01% to 0.5% by weight. Based on the weight of the feed and the medicated feed administered over prolonged periods. This could be in the nature of a preventive or prophyactic measure. Another method of administering the compounds of this invention to animals whose feeds are conveniently pelleted such as sheep is to incorporate them directly into the pellets. For instance, the anthelmintic compounds are readily incorporated in the nutritionally adequate alfalfa pellets at levels of 2 to 10 g. per pound for therapeutic use and lower levels for prophylactic use, and such pellets fed to the animals.

Examples of compositions suitable for administration to animals are:

A typical bolus composition is as follows:

---

4-Amino-6-trichlorovinyl-1,3

| -continued | |
|---|---|
| benzenedisulfonamide | 7.0 g. |
| Dicalcium phosphate | 1.0 g. |
| Starch | 0.7 g. |
| Guar gum | 0.16 g. |
| Talc | 0.11 g. |
| Magnesium stearate | 0.028 g. |

A typical drench composition is as follows:

| | |
|---|---|
| 4-Amino-6-($\alpha,\beta$-dichloro-$\beta$-fluorovinyl)-1,3-benzenedisulfonamide. | 5.0 g. |
| Benzalkonium chloride | 5.6 ml. |
| Antifoam emulsion | 0.06 g. |
| Hydroxyethyl cellulose | 0.3 g. |
| Sodium phosphate | 0.3 ml. |
| Water | q.s. to 30 ml. |

Examples of typical feed premix supplements are as follows:

| | | |
|---|---|---|
| A. | 4-Amino-6-trifluorovinyl-1,3-benzenedisulfonamide | 10 lbs. |
| | Wheat shorts | 90 lbs. |
| B. | 4-Amino-6-(1,1-dichloro-prop-1-ene-2-yl)-1,3-benzene-disulfonamide | 15 lbs. |
| | Ground oyster shells | 40 lbs. |
| | Citrus meal | 45 lbs. |
| C. | 4-Amino-6-(1,2-dichloro-3,3,3-trifluoropropenyl)-1,3-benzenedisulfonamide | 10 lbs. |
| | Corn meal | 90 lbs. |
| D. | 4-Amino-6-(1,2-dichloro-1-propenyl)-1,3-benzene-disulfonamide | 15 lbs. |
| | Wheat shorts | 50 lbs. |
| | Corn meal | 35 lbs. |

The above feed premix supplements are combined with the animals regular feed, intimately mixing therewith such that the final concentration of the active ingredient is from 0.01 to 3% by weight.

EXAMPLE 1A

4-Amino-6-(1,2,2-trichlorovinyl)-1,3,-benzenedisulfonamide 32.8 G. of 2-(3-aminophenyl)-1,1,2-trichloro ethylene is added dropwise with stirring to 107 ml. of chlorosulfonic acid maintained at +10° C. When the addition is completed, the reaction mixture is heated to 125°–130° and stirred at this temperature for 2 ½ hours. Then it is cooled to 20° C. and 40.2 ml. of thionylchloride is added in portions. After this, the reaction mixture is stirred at 80° C. for 1 ½ hours and then cooled in ice to +10° C. The reaction mixture is poured onto ice and the 4-amino-6-(1,2,2-trichlorovinyl)-1,3-benzenedisulfonylchloride is extracted into methylene chloride, washed with water, dried over MgSO$_4$ and concentrated in vacuo to 52 g. of a brown foam. The brown solid is dissolved in 60 ml. of CH$_2$Cl$_2$ and added in portions to 250 ml. of liquid ammonia. The excess ammonia and the methylene chloride are allowed to evaporate overnight. Water is added to the residue, and it is carefully acidified with concentrated HCl, giving an amorphous precipitate. This is extracted into ethyl acetate, washed with water, dried over MgSO$_4$ and concentrated in vacuo to 45 g. of brown foam. This is extracted twice with hot benzene leaving 38.5 g. of brown solids. The residue is extracted three times by boiling with 1000 ml. portions of ether, and the ether solutions are concentrated in vacuo to 250 ml., and crystalline product is precipitated by careful addition of hexane giving after filtration 20.8 g. of product — ether complex with melting point of 130°–135°. This is boiled with 175 ml. of water, without dissolving much of the compound for ½ hour then allowed to come to room temperature, filtered washed with water, dried in vacuo at 50° C. to give 17.0 g. of 4-amino-6-(1,2,2-trichlorovinyl)-1,3-benzenedisulfonamide with m.p. 188°–193° C. A small sample is recrystallized for analysis from aqueous methanol to melt at 205°–207°.

EXAMPLE 1B

4-Amino-N$^1$, N$^3$-dimethyl-6-(1,2,2-trichlorovinyl)-1,3-benzenedisulfonamide 10G. of 4-amino-6-(1,2,2-trichlorovinyl)-1,3-benzenedisulfonylchloride prepared as in example 1A is added to 150 ml. of liquid methylamine at −78° C. When the addition is completed, the cooling bath is removed and the excess methylamine is allowed to evaporate. The solid residue is taken up in water and acidified with acetic acid. A dark precipitate is collected by filtration and dried to give 7.4 g. of crude product. Purification by chromatography on a silica gel column and crystallization from ethanol gives 2.9 g. of 4-amino-N$^1$, N$^3$-dimethyl-6-(1,2,2-trichlorovinyl)-1,3-benzenedisulfonamide with a m.p. of 211° to 212° C.

EXAMPLE 1C

4-Amino-N$^1$, N$^1$, N$^3$, N$^3$-tetramethyl-6-(1,2,2-trichlorovinyl)-1,3-benzenedisulfonamide 10 G. of 4-amino-6-(1,2,2-trichlorovinyl)-1,3-benzenedisulfonylchloride prepared as in example 1A is treated with 125 ml. of dimethylamine. The reaction mixture is worked up in a manner similar to example 1B affording 5.2 g. of pure 4-amino-N$^1$, N$^1$, N$^3$, N$^3$-tetramethyl-6-(1,2,2-trichlorovinyl)-1,3-benzenedisulfonamide with a m.p. of 238° to 239° C.

EXAMPLE 2

4-Amino-6-(1,1-dichloroprop-1-en-2-yl)sulfonamide a. 1,1-dichloro-2-phenyl-1-propene A mixture of 30 g. of acetophenone, 420 ml. of CCl and 196 g. of triphenylphosphine is stirred at 60° C. for 9 hours. Then the liquid is decanted and the gummy residue washed well with ether. The solutions are combined and the CCl$_4$ and ether is distilled out through a short vigreaux column. The residue is distilled in vacuo at 35 mm. Hg. pressure and the fraction boiling at 120° C. is collected, representing 35.0 g. of 1,1-dichloro-2-phenyl-1-propene.

b. 1,1-dichloro-2-(4-nitrophenyl)-1-propene

A mixture of 33 ml. of concentrated H$_2$SO$_4$ and 28 ml. of concentrated HNO$_3$ (70%) is stirred in an ice bath while 35.0 g. of 1,1-dichloro-2-phenyl-1-propene is added, keeping the reaction mixture. between 10° and 20° C. It is allowed to come to room temperature and vigorous stirring is continued for 1 hour. It is poured onto ice, extracted with ether, the ether extract washed with water several times, dried over MgSO$_4$ and concentrated in vacuo. Vapor phase chromatography of the crude product indicates a mixture of two components presumably 1,1-dichloro-2-(4-nitrophenyl)-1-propene (major product) and its 2-nitro-isomer. The residue is distilled in vacuo at 1.0 mm. Hg. pressure and a 20.9 g. fraction with boiling point 147°–153° C. is collected.

c. 1,1-dichloro-2-(4-acetylaminophenyl)-1-propene 30.0 G. of iron powder is added to a solution of 29.7 g. of 1,1-dichloro-2-(4-nitrophenyl)-1-propene in 500 ml. of 50% aqueous ethanol and stirred vigorously at reflux temperature. A solution of 2.2 ml. of concentrated HCl in 10.0 ml. of 50% aqueous ethanol is added dropwise and the mixture is refluxed for a total of 40 minutes, filtered hot and cooled to room temperature. 500 Ml. of chloroform is added, it is made basic with a little aqueous NaHCO$_3$ solution and the layers are separated. The chloroform-alcohol layer is washed with water, dried over MgSO$_4$ and concentrated in vacuo to 28.5 g. of crude 1,1-dichloro-2-(4-aminophenyl)-1-propene. This is dissolved in 145 ml. of pyridine and stirred in an ice bath while 85 ml. of acetic anhydride is added over 5 minutes, then kept overnight at room temperature. Next morning it is concentrated in vacuo and high vacuo to a crystalline residue. 30 Ml. of ethyl acetate is added and the slurry is stirred 30 minutes at room temperature and 60 minutes in an ice bath. Then it is filtered, washed with little ethyl acetate and ether and dried in vacuo to give 18.0 g. of 1,1-dichloro-2-(4-acetylamino phenyl)-1-propene with m.p. 164.5° to 165.5°.

d. 1,1-dichloro-2-(4-acetylamino-3-nitrophenyl)-1-propene 6.0 G. of 1,1-dichloro-2-(4-acetylamino phenyl)-1-propene is dissolved in 120 ml. of acetic anhydride with stirring at 50° C., then quickly cooled to +5° C. affording a fine suspension. Then a mixture of 1.44 ml. of acetic anhydride and 4.28 ml. of concentrated HNO$_3$ previously prepared at −20° C. is added slowly over 50 minutes. Then the ice bath is replaced by an oil bath and the reaction mixture is heated over 30 minutes to 50° C., when everything is dissolved, kept 30 additional minutes at 50° C. and then cooled in an ice bath for 2 hours. Then the yellow crystalline precipitate is filtered, washed well with water and dried in vacuo to afford 3.14 g. of product with m.p. 142°-143°. The above filtrate is poured into water, stirred for 1 hour, the precipitate filtered, washed with water, dried in vacuo to give 2.40 g. additional 1,1-dichloro-2-(4-acetylamino-3-nitro phenyl)-1-propene of m.p. 139°-141°.

e. 1,1-dichloro-2-(4-amino-3-nitrophenyl)-1-propene

A suspension of 7.55 g. of 1,1-dichloro-2-(4-acetylamino-3-nitro phenyl)-1-propene in 150 ml. of 6 n. HCl is stirred and heated at reflux for 30 minutes. It is cooled in ice bath, made basic with 50 ml. of 50% aqueous NaOH and extracted with ethyl acetate. The extract is washed with water, dried and concentrated in vacuo to give 6.6 g. of crude 1,1-dichloro-2-(4-amino-3-nitro phenyl)-1-propene as a brown oil.

f. 2-nitro-4-(1,1-dichloroprop-1-en-2-yl)benzenedisulfonamide 4.1 Ml. of acetic acid is saturated with SO$_2$, 100 mg. of CuCl$_2$.2H$_2$O dissolved in 2 drops of water is added, and SO$_2$ is bubbled into the solution, which is maintained at 10° C. In a second flask, 500 mg. of 1,1-dichloro-2-(4-amino-3-nitro phenyl)-1-propene is stirred in 3.6 ml. of concentrated HCl and warmed to about 80° and then quickly cooled in ice. This suspension is stirred at 0°-5° C., while a solution of 170 mg. of NaNO$_2$ in 0.6 ml. of water is added slowly over 30 minutes and then the mixture is kept at 0° for 1 additional hour. Then 100 mg. of sulfamic acid is used to destroy the excess of NaNO$_2$. The reaction mixture is separated from some insoluble material by centrifugation and the clear solution is added rapidly to the acetic acid/SO$_2$/CuCl$_2$ solution prepared before at 10° C. It is allowed to come to room temperature over 30 minutes, then poured onto ice, extracted with methylene chloride, washed twice with water, dried and concentrated in vacuo to 350 mg. orange crystalline residue of 2-nitro-4-(1,1-dichloro-prop-1- n-2-yl)benzenesulfonylchloride. This is dissolved in about 10ml. of liquid ammonia and left overnight. To this is added 4 ml. of water and a few drops of 2.5 n. HCl, aged for 1 hour at room temperature, the solid is separated by centrifugation, washed with some water and dried to give 280 mg. of crystalline 2-nitro-4-(1,1-dichloroprop-1-en-2-yl)benzenedisulfonamide. A part of this is recrystallized from benzene-hexane to afford an analytical sample of the product with m.p. 149° to 151°.

g. 2-Amino-4-(1,1-dichloroprop-1-en-2-yl)benzenesulfonamide 1.02 G. of 2-nitro-4-(1,1-dichloroprop-1-en-2-yl) benzenedisulfonamide is dissolved in 30 ml. of 50% aqueous ethanol at about 70° C. While vigorously stirring, 1.0 g. or iron powder is added and the reaction mixture is heated to reflux. Three drops of concentrated HCl are added and the reflux is continued for 30 minutes, when the hot reaction mixture is filtered, the solution cooled to room temperature, 60 ml. of HCl and 15 ml. of ethanol is added, the organic layer is washed with water, dried and concentrated in vacuo to 980 mg. of light oil, which crystallizes from benzene petroleum benzene to give 410 mg. 2-amino-4-(1,1-dichlorprop-1-en-2-yl)benzenesulfonamide with m.p. 93° to 5° C.

h. 4-Amino-6-(1,1-dichloroprop-1-en-2-yl)-1,3-benzenedisulfonamide

100 Mg. of the 2-amino-4-(1,1-dichloroprop-1-en-2-yl)benzenesulfonamide and 1.0 ml. of chlorosulfonic acid is mixed at 5° to 10° C. and then immersed into an oil bath of 100° to 110° for 1 hour. The reaction mixture is cooled in ice, added onto ice, extracted into CH$_2$Cl$_2$, the solution is washed twice with water, dried and concentrated in vacuo to yield 75 mg. of crude 4-amino-6-(1,1-dichloroprop-1-en-2-yl)-1,3-benzenedisulfonylchloride, identified by nuclear magnetic resonance and mass spectral analyses. 100 Mg. of this disulfonylchloride is then dissolved in 4 ml. of tertbutanol and ammonia gas is bubbled into the solution for about 10 minutes at room temperature. It is kept at room temperature for 15 minutes and then concentrated in vacuo. The residue is dissolved in ethyl acetate, washed with dilute aqueous HCl, water, dried and concentrated in vacuo to 87 mg. of crude product which slowly crystallized. It is recrystallized from a methanol-benzene-methylene-chloride mixture to give 4-amino-6-(1,1-dichloroprop-1-ene-2-yl)-1,3-benzenedisulfonamide with m.p. 199° to 202° C.

i. 4-Amino-6-(1,1-dibromo-1-pent-en-2-yl)-1,3-benzenedisulfonamide

In example (2a) 37 g. of butyrophenone is substituted for the acetophenone and the carbon tetrachloride is replaced by carbon tetrabromide. Successively the same procedures are employed as set forth in examples (2a) through (2h) to give 4-amino-6-(1,1-dibromo-1-penten-2-yl)-1,3-benzenedisulfonamide.

j. 4-Amino-6-(3,3,3-trifluoropropynyl) 1,3-benzenedisulfonamide

Following the procedures of Examples (2b) through (2h) utilizing 3,3,3-trifluoro-1-phenylpropyne in place of 1,1-dichloro-2-phenyl-1-propene there is obtained 4-amino-6-(3-3-3-trifluoropropynyl) 1,3-benzenedisulfonamide.

EXAMPLE 3

4-Amino-6-(2-chloro-1,2-difluorovinyl)-1,3-benzenedisulonamide a. (1,2-Difluoro-1,2,2-trichloroethyl) benzene A solution of 86 g. of β-chloro-β, α-difluoro styrene in 200 ml. of $CCl_4$ chlorinated at room temperature with chlorine for 22 hours. The reaction mixture is then washed with water and aqueous sodium bicarbonate solution, dried over magnesium sulfate and concentrated by distillation of the solvent at atmospheric pressure through a vigreaux column. The liquid residue is then distilled in vacuo at 20 mm. Hg. pressure to give 100 g. of (1,-difluoro-1,2,2-trichloroethyl) benzene boiling at 96°-7°, $N_D25$-1.5073.

b. 3-(1,2-Difluoro-1,2,2-trichloroethyl)-nitrobenzene

100 G. of (1,2-difluoro-1,2,2-trichloroethyl) benzene is added dropwise over 30 mm. to a vigorously stirred nitration mixture of 80 ml. of concentrated nitric acid in 400 ml. of concentrated sulfuric acid while the temperature is maintained between 15° and 25° C. by cooling with an ice bath. When the addition is completed, stirring is continued at room temperature for 5 hours. It is then poured onto ice, and the product is extracted with methylenechloride. This solution is washed with water and aqueous sodium bicarbonate solution, dried and concentrated in vacuo to a yellow oil. The oily residue is distilled in vacuo to 2.2 mm. mercury pressure to give 104 g. of 3-(1,2-difluoro-1,2,2-trichloroethyl)-nitrobenzene with boiling point 122°-4°.

c. 3-(1,2-Difluoro1,2,2-trichloroethyl)-aniline 104.4 G. of 3-(1,2-difluoro-1,2,2-trichloroethyl)-nitrobenzene is added over 10 min. to a solution of 325 g. of crystalline stannous chloride ($SnCl_2 \cdot 2H_2O$) in 325 g. of concentrated HCl and 325 g. of ethanol with vigorous stirring, maintaining the temperature at 50° C. Stirring is continued for 3 additional hours. It is cooled in ice, and the precipitate collected by filtration. The solids are then suspended in 500 ml. water and 500 ml. of $CH_2Cl_2$, the mixture is cooled in ice and made basic by the addition of 50% aqueous NaOH until almost all solids are dissolved. The methylenechloride layer is separated, washed with water, dried with $Na_2SO_4$ and concentrated in vacuo to 75 g. of 3-(1,2-difluoro-1,2,2-trichloroethyl)-aniline as yellow oil.

d. 3-(2-Chloro-1,2-difluorovinyl)aniline

74 G. of zinc dust is added to a vigorously stirred solution of 40 g. of 3-(1,2-difluoro-1,2,2-trichloroethyl)-aniline in 450 ml. of ethanol and heated at reflux for 2 hours. It is filtered hot, the solid residue washed with hot ethanol and the combined ethanol solution cooled to room temperature. About 1000 ml. of chloroform is added and the organic layer is washed with aqueous $NaHCO_3$ solution and with water, dried over $Na_2SO_4$ and concentrated in vacuo to 23.9 g. of oily 3-(2-chloro-1,2-difluorovinyl)aniline. This gives a single peak with a retention time of 1.8 minutes at 200° C. on a gas liquid chromatography column packed with 5% SE30, and the correct values for C,H,N,Cl and F by combustion analysis.

e. 4-Amino-6-(2-chloro-1,2-difluorovinyl)-1,2-benzenedisulfonamide 2.0 G. of 3-(2-chloro-1,2-difluorovinyl) aniline added dropwise to 20 ml. of ice cold and well stirred chlorosulfonic acid. The 20 g. of dry sodium chloride is added in portions over 30 minutes at room temperature. The reaction flask is immersed in an oil bath and heated at 115° to 120° C. for 4 hours. It is cooled in ice and added in portions to ice water. This is treated with methylenechloride, the organic layer washed with water, dried and concentrated in vacuo to give crude 4-amino-6-(2-chloro-1,2-difluorovinyl)-1,3-benzenedisulfonylchloride, identified by a molecular ion peak of 385 in the mass spectrum with the characteristic pattern expected for a trichloro compound. This is immediately added to liquid ammonia and left overnight, while the excess ammonia is allowed to evaporate. The residue is dissolved in a small amount of water, acidified with dilute HCl and extracted with ethyl acetate, dried and concentrated in vacuo to 600 mg. of crude 4-amino-6-(2-chloro-1,2-difluorovinyl)-1,3-benzenedisulfonamide.

The nuclear magnetic resonance spectrum shows the two single peaks at 7.35 and 8.25 δ which are expected for this product, representing the protons at the 5 and 2 position of the 1,3,4,6-tetrasubstituted benzene ring. Further purification of this product by preparative layer chromatography on 2.0 mm. thick layers of silica gel with a benzene-ethyl acetate-(1:1)-mixture as liquid phase gave 210 mg. of pure product, which gave from methylenechloride-ether mixture white crystals, m.p. 184°–187° C., and a molecular ion of 347 by mass spectrometry.

EXAMPLE 4

4-Amino-6-(2,2-dichlorovinyl)-1,3-benzenedisulfonamide a. ββ-dichloro-3-nitrostyrene A solution of 32.8 g. of triphenylphosphine in 70 ml. of carbon tetrachloride is stirred for 3 hours at 60° C. to prepare in situ the reagent triphenylphosphine dichloromethylene. A solution of 18.9 g. of 3-nitro benzaldehyde in 60 ml. of carbon tetrachloride is added and the mixture is continued to be stirred at 60° C. for an additional 2 hours, when vapour phase chromatography indicates that all the starting 3-nitrobenzenealdehyde has disappeared and two new peaks in a ratio of 1:1 show the formation of a mixture of ββ-dichloro3-nitrostyrene and 3-nitrobenzalchloride. The reaction mixture is decanted from the solid residues and concentrated in vacuo to an oil. This is treated with ether, and again separated from some solid precipitate and the solution is again concentrated in vacuo. The oily residue is then carefully distilled in high vacuo to give essentially pure β,β-dichloro-3-nitrostyrene.

b. β, β-dichloro-3-aminostyrene 26.4 G. of β, β-dichloro-3-nitrostyrene is reduced accoring to the procedure of example (2c) to give the corresponding β, β-dichloro-3-aminostyrene compound.

c. 4-Amino-6-(2,2-dichlorovinyl)-1,3-benzenedisulfonamide 2.0 G. β, β-dichloro-3-aminostyrene is added dropwise to 20 ml. of ice cold chloro sulfonic acid. As soon as the addition is complete, the reaction flask is immersed in preheated oil bath of 110° C. and kept there for 1 hour. It is then removed from the oil bath and cooled in an ice bath. Then the reaction mixture is added dropwise to a large excess of ice water and the disulfonychloride is extracted with methylenechloride, the methylenechloride solution is dried over magnesium sulfate and concentrated in vacuo to about 5 ml. This concentrated solution is added dropwise to about 50 ml. of liquid ammonia and left overnight at ambient temperature. It is taken up the next morning in little water, acidified with dilute HCl, and extracted with ethyl acetate. The extract is dried over magnesium sulfate and concentrated in vacuo to a gummy residue. 200 Mg. of this residue is dissolved in about 5 ml. ethyl acetate and applied to a preparative layer chromatography plate 20 × 20 cm size and coated with a 2.0 mm. layer of silica gel. Development with a benzene-ethylacetate 1:1 mixture and extraction of one bandrepresenting the product gives essentially pure 4-amino-6-(2,2-dichlorovinyl)-1,3-benzenedisulfonamide.

EXAMPLE 5

1,2-Dichloro-1-(5-amino-2,4-disulfamylphenyl)-propene a. 1,1,2,2-Tetrachloro-1-(3-nitrophenyl)propane

47 G. of 1,1,2,2,-tetrachloro-1-phenyl-1-propane is added dropwise over 45min. to a well stirred nitration mixture of 31.2 ml. of concentrated sulfuric acid and 16.9 ml. of concentrated nitric acid while the temperature is maintained between 25° and 35° C. Stirring is continued for 3 additional hours at room temperature when the reaction mixture is poured onto ice water, extracted with $CH_2Cl_2$, concentrated in vacuo and crystallized from 125 ml. of methanol to give 29 g. of yellow crystalline 1,1,2,2-tetrachloro-1-(3-nitrophenyl) propane with m.p. 75.5 to 77° C.

b. 1,2-Dichloro-1-(3-aminophenyl)-1-propene

13 G. of 1,1,2,2-tetrachloro-1-(3-nitrophenyl) propane and 7.9 g. of iron powder is stirred vigorously under reflux in 465 ml. of 50% aqueous ethanol. 5.6 Ml of a solution prepared prejviously from 52 ml. of concentrated hydrochloric acid and 250 ml. of 50% aqueous ethanol are added dropwise over 5 minutes. After an additional 2 hours of stirring at reflux temperature, the hot reaction mixture is filtered, cooled to room temperature, diluted with enough chloroform to double the volume of the ethanol, and made basic with saturated aqueous sodium bicarbonate solution. The organic layer is separated, washed with water, dried and concentrated in vacuo to give a mixture of essentially pure cis and trans 1,2-dichloro-1-(3-aminophenyl)-1-propene as a yellow oil.

c. 1,2,-dichloro-1-(5-amino-2,4-disulfamylphenyl)-1-propene 1.0 G. of 1,2-dichloro-1-(3-aminophenyl)-1-propene is added dropwise to 13 ml. of ice cold chlorosulfonic acid, followed by 13 g. of dry sodium chloride NaCl over 35 minutes. The reaction mixture is heated up to 125 ° C. over 30 minutes and kept at this temperature for 1 ½ hours. It is cooled poured onto ice water, extracted with methylene chloride, dried over magnesium sulfate and concentrated in vacuo to 900 mg. of crude intermediate disulfonylchloride. This is added to liquid ammonia and left overnight. The crude disulfonamide is isolated by addition of water, acidification with dilute HCl, extraction with ethylacetate and evaporation of the extract in vacuo. Further purification by preparative layer chromatography on silica gel coated plates gave 40 mg. of essentially pure 1,2-dichloro-1-(5-amino-2,4-disulfonylphenyl)-1-propene.

EXAMPLE 6

4-Amino-6-(1,2-dichlorovinyl)-1,3-benzenedisulfonamide a. 1,1,2-Trichloro-2-(3-nitrophenyl)ethane 13.8 G. of 3-nitroaniline are dissolved in a hot mixture of 30 ml. of concentrated HCl and 30 ml. of water, cooled to room temperature, and 80 g. of ice is added. Under vigorously stirring 24 ml. of a 30% aqueous sodium nitrate solution is added rapidly. Powdered sodium bicarbonate is added to this solution until the pH is about 2, then the reaction mixture is cooled to 0° C. This diazonium solution is added to a well stirred solution of 20 g. of trans-1,2-dichloroethylene in 75 ml. of acetone and 2.1 g. of cupricchloride dihydrate and .75 g. of calcium oxide at 0°-2° C. When addition is completed, the reaction mixture is allowed to come to room temperature and stirred overnight. Workup is accomplished by addition of methylene chloride, separation of the organic layer, and concentration to a crude mixture of 1,1,2-trichloro-2-(3-nitrophenyl)ethane and 3-chloronitrobenzene from which the product is isolated by fractional distillation in high vacuo.

b. 1,2-Dichloro-2-(m-nitrophenyl)ethylene

A solution of 2.5 g. KOH in 30 ml. of ethanol is added from a dropping funnel to a solution of 9.0 g. of 1,1,2-trichloro-2-(3-nitrophenyl)ethane in 20 ml. of ETOH during 20 minutes and after that the reaction mixture is boiled in the steam bath for 2 hours. It is cooled to room temperature poured an 100 ml. of water and extracted with ether. After removel of the ether in vacuo the residue is distilled in high vacuo to yield pure 1,2-dichloro-2-(m-nitrophenyl)ethylene.

c. 1,2-Dichloro-2-(m-aminophenyl)ethylene 10.0 G. of iron powder is added to a solution of 8.7 g. of 1,2-dichloro-2-(m-nitrophenyl)ethylenein 170 ml. of 50% aqueous ethanol and reduced analogous to procedure 2c) to give crude 1,2-dichloro-2-(m-aminophenyl) ethylene suitable for use in the next step.

d. 4-Amino-6-(1,2-dichlorovinyl)-1,3-benzenedisulfonamide 1.0 G. of 1,2-dichloro-2-(m-aminophenyl)ethylene is added dropwise to 10 ml. of cold chlorosulfonic acid followed by 10 g. of sodium chloride. The chlorosulfonation workup and treatment with liquid ammonia is carried out as described in example (3e) to give the 4-amino-6-(1,2-dichlorovinyl)-1,3-benzenedisulfonamide.

EXAMPLE 7

4-Bromo-6-(1,2,2-trichlorovinyl)-1,3-benzenedisulfonamide

Nitrosyl sulfuric acid is prepared by addition of 0.51 g. of powdered $NaNO_2$ to 6.0 ml. cold (0°), well stirred concentrated $H_2SO_4$. Then 2.53 g. of 4-amino-6-trichlorovinyl-1,3-benzene disulfonamide is added in portions, followed by 6.0 ml. of glacial acetic acid. The reaction mixture is then stirred for 15 minutes at 15° C. to complete the diazotization reaction. A solution of 1.2 g. of cuprous bromide ($Cu_2Br_2$) in 6.0 ml. of concentrated hydrobromic acid is then added dropwise and the reaction mixture is heated on a steam bath for 30 minutes after completion of the addition. Addition of the reaction mixture to 200 ml. of cold water results in a precipitate, which is collected by filtration and dried to give 1.11 g. of essentially pure 4-bromo-6-(1,2,2-trichlorovinyl)-1,3-benzenedisulfonamide which after one recrystallization from ethylacetate/benzene gives 0.86 g. pure product with a m.p. of 228°-229° C.

EXAMPLE 7A

4-Chloro-6-(1,2,2-trichlorovinyl)-1,3-benzenedisulfonamide

If cuprous chloride and concentrated HCl in the above procedure is substituted for the cuprous bromide and concentrated HBr respectively, 0.76 g. of 4-chloro-6-(1,2,2-trichlorovinyl)-1,3-benzenedisulfonamide is obtained which melts after one recrystallization from ethylacetate/benzene at 211°-213° C. (dec.)

EXAMPLE 7B

4-Chloro-$N^1$, $N^3$-dimethyl-6-(1,2,2-trichlorovinyl)-1,3-benzenedisulfonamide The title compound is obtained if 4-amino-$N^1$, $N^3$-dimethyl-6-trichlorovinyl-1,3-benzenedisulfonamide is used in the procedure of Example 7 as the amino compound in place of 4-amino-6-trichlorovinyl-1,3-benzenedi-sulfonamide.

EXAMPLE 8

4-Benzylamino-6-(1,2,2-trichlorovinyl)-1,3-benzenedisulfonamide

A mixture of 0.31 g. of 4-bromo-6-trichlorovinyl-1,3-benzenedisulfonamide and 0.76 ml. of benzylamine is stirred at 100° C for 2 hours and then added to 25 ml. of aqueous acetic acid and cooled in ice. A precipitate is collected by filtration which weighs 0.26 g. after drying, which gives after recrystallization from a ethylacetate/benzene/petroleum benzene mixture 0.17 g. of 4-benzylamino-6-(1,2,2-trichlorovinyl)-1,3-benzenedisulfonamide with m.p. 188°-190° C.

EXAMPLE 9

4-Furfurylamino-6-(1,2,2-trichlorovinyl)-1,3-benzenedisulfonamide

4-Bromo-6-trichlorovinyl-1,3-benzenedisulfonamide and furfurylamine are reacted at 70° C. for 10 hours in analogy to above procedure to give 4-furfurylamino-6-(1,2,2-trichlorovinyl)-1,3-benzenedisulfonamide with m.p. 155°-155° C.

EXAMPLE 10

4-Methylamino-6-(1,2,2-trichlorovinyl)-1,3-benzenedisulfonamide

A mixture of 0.445 g. of 4-bromo-6-trichlorovinyl-1,3-benzenedisulfonamide, 15 ml. of methanol and 5 to 10 ml. of methylamine is sealed in a steel tube and heated to 45° C. for 2 hours. The reaction mixture is then concentrated to a solid residue which is triturated with aqueous acetic acid. This mixture is extracted with ethylacetate and again concentrated in vacuo to 0.3 g. of an amorphous solid. Crystallization from aqueous methanol gives 60 mg. of 4-methylamino-6-(1,2,2-trichlorovinyl)-1,3-benzenedisulfonamide m.p. 239°-240° C. (dec.).

If the nucleophilic amino component in the previous examples is replaced by isopropylamine, di-n-butylamine, N-methylpiperazine, morpholine, thiomorpholine 1,1-dioxide, or aniline the corresponding 4-isopropylamino; 4-N,N-di-n-butylamino; 4-(4-methylpiperazinyl);4-(4-morpholinyl);4-(1,1-dioxy-4-thiomorpholinyl); or 4-phenylamino-6-trichlorovinyl-1,3-benzenedisulfonamides are obtained.

What is claimed is:

1.

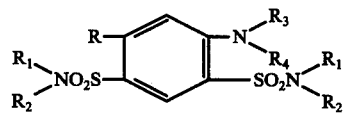

wherein $R_1$ and $R_2$ are each independently hydrogen or lower-alkyl; R is a halogenated unsaturated alkyl group containing from 2 to 6 carbon atoms, one or two double bonds or a single triple bond, and from 1 to 11 halogen atoms; and $R_3$ and $R_4$ are independently hydrogen, loweralkyl, benzyl, or phenyl.

2. The compound of claim 1 wherein R is a carbon chain of from 2 to 4 carbon atoms containing a single double bond and from 2 to 6 halogen atoms.

3. The compound of claim 2 wherein the halogen atoms of the R group are chlorine, fluorine of a mixture thereof.

4. The compound of claim 3 which is 4-amino-6-trichlorovinyl-1,3-benzenedisulfonamide.

5. The compound of claim 3 which is 4-amino-6-($\alpha,\beta$-difluoro-$\beta$-chlorovinyl)-1,3-benzenedisulfonamide.

6. The compound of claim 3 which is 4-amino-6-($\alpha,\beta$-dichloro-$\beta$-fluorovinyl)-1,3-benzenedisulfonamide.

7. The compound of claim 3 which is 4-amino-6-trifluorovinyl-1,3-benzenedisulfonamide.

8. The compound of claim 1 which is 4-amino-6-(1,1-dichloroprop-1-ene-2-yl)-1,3-benzenedisulfonamide.

9. The compound of claim 1 which is 4-amino-6-(1,2-dichloro-3,3,3-trifluoropropenyl)-1,3-benzenedisulfonamide.

10. The compound of claim 1 which is 4-amino-6-(1,2-dichloropropenyl)-1,3-benzenedisulfonamide.

11. The compound of claim 3 is $N^1,N^3$-dimethyl-6-(1,2,2-trichlorovinyl)-1,3-benzenedisulfonamide.

12. An anti-liver fluke composition which comprises an inert carrier and an effective amount of a compound having the formula:

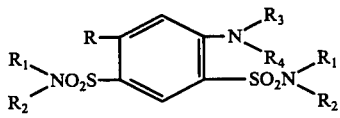

wherein each $R_1$ and $R_2$ is independently hydrogen or loweralkyl; R is a halogenated unsaturated alkyl group containing from 2 to 6 carbon atoms, one or two double bonds or a single triple bond, and from 1 to 11 halogen atoms; and $R_3$ and $R_4$ are independently hydrogen, loweralkyl, benzyl, or phenyl.

13. A method for the treatment of liver fluke infections which comprises administering to an animal infected with liver flukes an effective amount of a compound having the

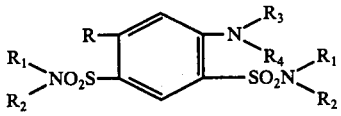

wherein $R_1$ and $R_2$ are each independently hydrogen or loweralkyl; R is a halogenated unsaturated alkyl group containing from 2 to 6 carbon atoms, one or two double bonds or a single triple bond, and from 1 to 11 halogen atoms; and $R_3$ and $R_4$ are independently hydrogen, loweralkyl, benzyl, or phenyl.

* * * * *